(12) United States Patent
Steiner (10) Patent No.: US 8,488,292 B2
(45) Date of Patent: Jul. 16, 2013

(54) MAGNETIC FIELD GENERATING MEANS

(75) Inventor: Rudolf Steiner, Geisenheim (DE)

(73) Assignee: GSI Helmholtzzentrum fuer Schwerionenforschung GmbH, Darmstadt (DE)

( * ) Notice: Subject to any disclaimer, the term of this patent is extended or adjusted under 35 U.S.C. 154(b) by 240 days.

(21) Appl. No.: 12/989,077

(22) PCT Filed: Apr. 21, 2009

(86) PCT No.: PCT/EP2009/002902
§ 371 (c)(1),
(2), (4) Date: Dec. 27, 2010

(87) PCT Pub. No.: WO2009/130002
PCT Pub. Date: Oct. 29, 2009

(65) Prior Publication Data
US 2011/0116200 A1    May 19, 2011

(30) Foreign Application Priority Data

Apr. 23, 2008 (DE) .......................... 10 2008 020 445
Nov. 18, 2008 (DE) .......................... 10 2008 057 815

(51) Int. Cl.
*H01H 47/00* (2006.01)

(52) U.S. Cl.
USPC .......................................... 361/143; 361/139

(58) Field of Classification Search
USPC .......................................... 361/139, 143, 144
See application file for complete search history.

(56) References Cited

U.S. PATENT DOCUMENTS

| | | | |
|---|---|---|---|
| 4,254,373 A * | 3/1981 | Lippmaa et al. | 324/321 |
| 4,788,502 A | 11/1988 | Keller et al. | |
| 5,365,174 A * | 11/1994 | Yoshikata et al. | 324/318 |
| 5,631,561 A | 5/1997 | Stetter | |
| 6,635,883 B2 | 10/2003 | Torti et al. | |
| 2006/0142748 A1 * | 6/2006 | Foreman et al. | 606/27 |

FOREIGN PATENT DOCUMENTS

| | | |
|---|---|---|
| DE | 44 19 061 A1 | 12/1995 |
| DE | 195 10 142 A1 | 9/1996 |
| DE | 197 02 831 A1 | 3/1998 |
| EP | 02 57 371 A2 | 3/1988 |
| EP | 08 99 576 A1 | 3/1999 |
| EP | 1 603 142 A1 | 12/2005 |
| WO | WO 2009/037709 A2 | 3/2009 |

OTHER PUBLICATIONS

International Search Report from PCT/EP2009/002982 dated Oct. 6, 2009.

* cited by examiner

*Primary Examiner* — Danny Nguyen
(74) *Attorney, Agent, or Firm* — Leydig, Voit & Mayer, Ltd.

(57) ABSTRACT

A magnetic-field generating device includes at least one magnetic-field generator configured to generate a magnetic field so as to provide at least one magnetic gap for receiving objects upon which the magnetic field acts. At least one magnetic-field measuring device is disposed within a measuring-device receiving region outside of the magnetic gap. The at least one magnetic-field measuring device is configured to provide at least one measurement signal useable as an input signal for controlling the at least one magnetic-field generator.

15 Claims, 8 Drawing Sheets

MAGNETIC FIELD GENERATING MEANS

CROSS-REFERENCE TO RELATED APPLICATIONS

This application is a U.S. National Phase application under 35 U.S.C. §371 of International Application No. PCT/EP2009/002902, filed on Apr. 21, 2009, and which claims the benefit of German Patent Application No. DE 10 2008 020 445.5, filed Apr. 23, 2008 and German Patent Application No. DE 10 2008 057 815.0, filed on Nov. 18, 2008. The International Patent Application was published in German on Oct. 29, 2009 as WO 2009/130002 A1.

FIELD

The present disclosure relates to a magnetic-field generating device having at least one magnetic gap for receiving objects upon which a magnetic field acts that is generated by at least one magnetic-field generating means of the magnetic-field generating device. The present disclosure also relates to a system having such a magnetic-field generating device. Moreover, the present disclosure also relates to a method for controlling such a magnetic-field generating device, respectively, to a method for controlling a system having such a magnetic-field generating device.

BACKGROUND

Apparatuses and devices, whose operation or function is largely based on generating strong, and, when indicated, also changing magnetic fields, are becoming more and more prevalent in the context of apparatuses that are used for manufacturing and maintenance purposes, or also in the medical field. This is also true of apparatuses, which, until a few years ago, were used exclusively for basic research purposes.

Particle accelerators for therapeutic purposes come to mind in this case, for example. Particle accelerators can be used, in particular, for purposes of tumor therapy. Even inoperable tumors, especially brain tumors, can be successfully treated with the aid of particle accelerators. These types of therapeutic particle accelerators not only use electrons as accelerated particles, but in recent times, ions (mostly carbon ions) as well. Not only are linear accelerators used as particle accelerators, but synchrotrons (accelerator rings) are as well.

Other examples of devices whose operation or function is largely based on generating strong, and, when indicated, also changing magnetic fields, are devices in the manufacturing sector, such as devices used in induction hardening, for example. The medical sector also includes other fields of application, such as NMR diagnostic imaging devices (NMR denoting "nuclear magnetic resonance").

While the cost effectiveness of a system is rather a low priority in pure research applications, in the manufacturing, maintenance and medical sectors, applications increasingly require a most economic possible operation of the systems.

Magnets in use today have the inherent problem of reproducibility of the magnetic fields. This is particularly true of magnets that are required to generate a time-variant magnetic field. Moreover, particularly when working with magnetic fields that change frequently and relatively quickly over time, the problem arises that a specific setpoint magnetic field is to be reached as quickly as possible.

For example, to provide a most economic operation of a synchrotron possible, it is desirable to achieve, on average over time, a highest possible percentage of the time for emission of the particle beam. This can be achieved by reducing to the greatest degree possible the time percentages in which the synchrotron is in the remaining operating modes. To this end, the time periods used for injecting and accelerating the particle beam in the synchrotron are kept as short as possible. This, in turn, requires keeping the amount of time needed to build up (ramp up), reduce (ramp down) and stabilize the magnetic fields used for beam deflection (dipole magnets) and beam focusing (quadrupole magnets) as short as possible.

Presently, in the case of particle accelerators, the magnets are generally controlled by current sources which apply current to the magnets at a predefined (typically time-variant) current intensity. To this end, what are generally referred to as DCCT (denotes "direct current to current transformers") have proven effective over the years. To ascertain the relationship between the current, which flows through the magnetic coils, and the magnetic field, laboratory measurements are first performed on the magnets. For each applied current intensity, the magnetic field prevailing in the magnet is measured. To this end, a suitable probe—in practice, mostly an NMR or a Hall-effect sensor—is used. The measurement data obtained are used to generate a characteristic map that is subsequently used to control the magnet. Since the magnetic field also changes within the magnet as a function of location, additional laboratory measurements are necessary to determine the location dependency.

The remanence of magnetic materials complicates the process of generating characteristic maps within the framework of laboratory measurements. Virtually without exception, the magnets (dipole magnets and quadrupole magnets) currently used in accelerator systems are electromagnets that have normal-conducting current coils having cores and yokes of soft magnetic material (mostly bonded together iron sheets). When the electromagnet generates a magnetic field in response to the application of electric current, the soft magnetic material is automatically magnetized. Even when the electric current is subsequently switched off, a residual magnetization of the soft magnetic material remains, which is generally known as remanence. Thus, a magnetic field also remains in the magnetic gap of the electromagnet. The remanence field strength is a static property and does not decay over time. In this context, the intensity of the remanence field strength is not only dependent on the materials and the configuration of the electromagnets, but also on the magnetization prehistory of the electromagnet, respectively of the soft magnetic material. Thus, a consistently same magnetic field strength cannot necessarily have a specific, constant magnet current value In assigned thereto.

To be able to deduce the magnetic field strength generated by the electromagnet from a specific magnet current value In, it is necessary to observe an established procedure to arrive at the magnet current value In. A defined magnetization prehistory is thereby obtained. This is described as "conditioning." Normal conditioning processes provide for controlling the magnet to its maximum value (and thus for driving the soft magnetic materials into saturation), and then subsequently reducing it to zero current, in order, from there, to approach the setting value. Following the conditioning process, the reproducibility of the magnetic field is typically better than $10^{-4}$ T (at maximum field strengths of typically 1.5 T to 2 T). For beam guidance magnets, the maximum remanence field Br is typically between $\pm 1 \cdot 10^{-3}$ T and $\pm 3 \cdot 10^{-3}$ T. For magnets having unipolar operation, the maximum remanence field Br is typically lower and is within the range of approximately $\pm 2 \cdot 10^{-4}$ T to $\pm 4 \cdot 10^{-4}$ T. The characteristic maps determined in the laboratory are based on this type of defined conditioning.

In the field of particle accelerators, remanence means that the preceding acceleration cycle(s) fundamentally influence(s) the properties of the magnet(s) in the subsequent acceleration cycle. Since in the case of particle accelerators, magnetic field variations of typically $2 \cdot 10^{-4}$ T to $4 \cdot 10^{-4}$ T play a critical role in determining beam loss or unacceptable changes in the beam properties, the ambiguity between the magnetic current and the generated magnetic field due to remanence is generally not tolerable.

Therefore, in the case of particle accelerators, a conditioning of the accelerator magnets has already been provided. A typical conditioning process provides for using what is generally referred to as a "chimney." In this case, at the end of a particle beam extraction cycle, the accelerator magnets are normally driven to saturation and are subsequently driven to zero current. This creates controlled initial conditions for the next acceleration cycle. The disadvantage is obvious: To ramp up the magnets, energy is consumed without deriving any actual benefit. Time is also required to ramp up the magnets to the saturation region (and to subsequently ramp them down). The required time period is all the greater, the lower the particle energy is in the preceding acceleration cycle.

Under certain circumstances, a conditioning can also be carried out using what are generally referred to as "training cycles." To this end, a defined magnetization prehistory of the magnets is made available, whereby it is not necessarily required that the magnets be ramped up to the saturation region. Such an approach can be appropriate when it is only rarely necessary to alter the particle energy of the particle beam. However, when the required magnetic field sequences deviate from the conditioning cycles, the use of training cycles is de facto not possible. Since, in practice, up to five (sometimes even more) training cycles are required, too much energy and beam time would then be lost. However, in medical applications, in particular, the particle energy must be changed very frequently. This is particularly true of raster scanning methods used for treating tumors.

Another source of ambiguities in the relationship between the magnet current and the magnetic field are the dynamic effects in the magnets when they generate rapidly time-variant magnetic fields. This is primarily caused by eddy currents. Conditioning is not effective in countering dynamic deviations. However, since the dynamic deviations decay over time, the errors can be reduced by waiting. In the case of a typical synchrotron magnet having a yoke of bonded together iron sheets, that is ramped in one second from zero to its full field (typically within the range of 1.5 T to 2 T), the initial store of the static end field is up to $\pm 3 \cdot 10^{-3}$ T. Thus, the initial dynamic store is within the range of the remanence errors or is greater than the same. In the case of bonded sheets, the decay time constant is normally within the range of 0.3 seconds. However, in the case of magnets made of solid iron, the decay time constant can also be within the range of many seconds.

SUMMARY

A satisfactory way to control magnets is still lacking in the case of machines that utilize high and time-variant magnetic fields, as is true of therapeutic synchrotrons or NMRs, for example. It is, therefore, an aspect of the present disclosure to provide improved magnetic-field generating devices, as well as systems which have at least one such magnetic-field generating device. It is an additional, alternative aspect of the present disclosure to provide an improved method for controlling such magnetic-field generating devices, and/or systems which have at least one such magnetic-field generating device.

In an embodiment, the present invention provides a magnetic-field generating device including at least one magnetic-field generator configured to generate a magnetic field so as to provide at least one magnetic gap for receiving objects upon which the magnetic field acts. At least one magnetic-field measuring device is disposed within a measuring-device receiving region outside of the magnetic gap. The at least one magnetic-field measuring device is configured to provide at least one measurement signal useable as an input signal for controlling the at least one magnetic-field generator.

BRIEF DESCRIPTION OF THE DRAWINGS

The present disclosure is clarified in greater detail in the following on the basis of advantageous exemplary embodiments and with reference to the enclosed drawings, whose figures show.

DETAILED DESCRIPTION

A magnetic-field generating device, which has at least one magnetic gap for receiving objects upon which a magnetic field acts that is generated by at least one magnetic-field generating means of the magnetic-field generating device, is provided in accordance with the present disclosure with at least one magnetic-field measuring means that is configured within a measuring-means receiving region located outside of the magnetic gap. This makes it possible to obtain precise knowledge of the current state of the magnetic field. This may possibly eliminate the need for measuring the characteristics in advance in the laboratory or, however, at least simplify the process. It is especially advantageous that, by directly measuring the magnetic field, the remanence, and thus the influence of the preceding acceleration cycles, may be recorded and thus taken into consideration in a particularly simple manner. In particular, this may eliminate the need for using a "chimney" or for training cycles, or they may at least be significantly limited. Using the magnetic-field measuring means, it is even possible to record and allow for magnetic field fluctuations that are caused by dynamic effects. For example, the currently measured value of the magnetic field strength in each case may be used to readjust the current that is used to excite the magnetic field, in accordance with the current measured value of the magnetic-field measuring means. This may be implemented by an appropriate control device. The magnetic-field measuring means may be used to measure the magnetic field, while the magnetic-field generating device is actively operated. In this context, the magnetic-field measuring means should measure the strength of the magnetic field preferably at an accuracy of $10^{-4}$, and more preferably of $10^{-5}$ relative to the design value of the magnetic-field generating device. The output signal of the magnetic-field measuring means may be used to carry out or influence the controlling of the magnetic-field generating device. This controlling, respectively influencing of the magnetic-field generating device makes it possible for magnetic fields—in particular, also strong magnetic fields—to be generated highly precisely in an especially rapid, temperature-stable and time-stable manner. For example, in the case of an electrically operated magnetic-field generating device, the current, which is used to control the magnetic-field generating device (respectively, the magnetic-field generating means), may be controlled or influenced. In place of a magnet current control that has been customary under known methods heretofore, a direct magnetic field control may be thereby realized. If, for example, the particle beam of a synchrotron is influenced (deflected and/or focused) with the aid of the magnetic-field generating device, then especially positionally accurate and/or particularly well focused particle beams may be reproducibly generated. By configuring the magnetic-field measuring means outside of the magnetic gap, the field may be measured by the magnetic-field measuring means within the course of a regular operation of the magnetic-field generating device, respectively of the system in which the magnetic-field generating device is used. In this context, the signal may be measured in a magnetic-field generating device that is built into the system—for example, into a synchrotron. Thus, the magnetic-field measuring means is not—as under the related art—best installed in a magnetic-field generating device that is spatially separate from the beam guidance of the synchrotron (and that is normally configured at a considerable distance from the actual synchrotron). Therefore, when a magnetic-field generating device having the design according to the present disclosure is used, the need for separate (laboratory) measurements (whether in separate devices and/or at separate points in time) may be eliminated, if indicated, or, however, they may at least be greatly reduced. It is self-evident that separately ascertained measured values may be used, as before, to perform "course control." A "subsequent fine adjustment" of the magnetic-field generating means (or of other devices, such as additional magnetic-field generating means, for example) may be carried out with the aid of measured values supplied by the magnetic-field measuring means. The objects may be objects that remain in the magnetic gap for relatively long periods of time (for example, patients in the case of a nuclear spin tomograph—"NMR") or even permanently (beam tube in the case of a synchrotron). However, it may also be a question of objects that are present in the magnetic gap for only a short period of time, as is true of the particles of a particle beam in the case of a synchrotron (or a different type of particle accelerator), for example. Within the scope of this document, a magnetic gap is understood to not only be the free width between the bounding surfaces of the magnetic-field generating device (for example, the pole shoes of a magnet), but also, in particular, what is commonly referred to as the aperture. The aperture is, in particular, the region that is provided for receiving the object to be acted upon by the magnetic field of the magnetic-field generating device ("exposure cavity"). Therefore, in the case of a magnetic-field generating device designed as an electromagnet, it would be conceivable in this sense for a magnetic-field measuring means to be configured on the end face of a pole shoe. It may, in some instances, also be considered as being included in the approach that the, respectively, at least one magnetic-field measuring means is located inside of the vacuum chamber of the synchrotron (and thus inside of the magnetic gap), however, outside of the area within which it is acceptable for the particle beam to be located during regular operation of the system. It is also noted here that a magnetic-field generating device may be understood to be the magnetic-field generating device including, but also without the auxiliary devices that are required for the proper functioning thereof. Therefore, in the case of a magnetic-field generating device having electrically operated coils, the magnet may be understood as such, but may also be understood as a combination of a magnet and a (controllable) power supply device.

The present disclosure also provides for the magnetic-field generating device to be designed to generate a time-variant magnetic field at least periodically. This may, in particular, be a magnetic-field generating device that is operated at least periodically in a pulsed mode and/or in a ramp mode, above all, when an especially broad dynamic range is to be covered in the process. Magnets for use in particle accelerators (in particular, synchrotrons) or nuclear spin tomographs (NMR) come to mind, for example. They are frequently required to generate magnetic fields having rising and trailing edges that alternate with constant plateaus, respectively, what are commonly known as "sweeps." It is especially true of such time-variant fields that the advantages derivable from a more precise knowledge of the strength of the magnetic field may be very significant. In particular, it is also possible to allow for the dynamic effects that may occur when working with such time-variant magnetic fields. In the case of the magnets for particle accelerators, beam-guidance magnets (dipoles), as well as beam-focusing magnets (quadrupoles) come to mind, in particular.

The magnetic-field generating device may be designed to include at least one dipole magnetic-field generating device and/or at least one quadrupole magnetic-field generating device. In this context, they may, in particular, be electrically operated dipole magnets and/or electrically operated quadrupole magnets that are preferably designed as magnets having normal-conducting current coils. In particular, the magnets, respectively the magnetic-field generating devices may have at least one yoke, respectively at least one magnetic core of a soft magnetic material. These types of magnetic-field generating devices are especially required for nuclear spin tomographs (NMRs) and particle accelerators, such as synchrotrons, in particular. In the case of a synchrotron, dipole magnetic-field generating devices are used for beam deflection, for example, while quadrupole magnetic field-generating devices are used for beam focusing. Since in the context of a synchrotron, many magnetic-field generating devices have the same particle beam packet pass through very frequently (for example, several hundred thousand times), it is very advantageous when the magnetic-field generating devices in question generate very precise magnetic fields. This is because even relatively small errors may add up over several cycles and lead to a loss of the particle beam, respectively, to such a degradation thereof that it is ultimately no longer usable. Magnetic-field generating devices that deviate therefrom are also conceivable, such as, in particular, magnetic-field generating devices having $2 \cdot n$ poles, whereby $n=3, 4, 5$ or 6 may also be considered, in particular.

One possible design of a magnetic-field generating device is provided by developing at least one magnetic-field measuring means as an induction measuring means, in particular as a conductor loop ("pick-up coil") and/or as a coil. Magnetic-field measuring means of this kind typically require only a very small space. Moreover, these types of magnetic-field measuring means may normally be adapted very simply and flexibly to a complex space. Moreover, such magnetic-field measuring means are typically cost-effective as well, normally exhibit no, respectively no significant temperature drift, and are mostly also characterized by an especially long service life, without being subject to any appreciable effects of aging. Another advantage of such magnetic-field measuring means is that they typically feature very rapid measurement capabilities. Such rapid measurement capabilities are typically very important, especially when the measurement signal generated by the magnetic-field measuring means is also to be used for a feedback process to readjust the control of the magnetic-field generating means. Finally, the magnetic-field measuring means in accordance with the present disclosure may also be used for environments where a higher electromagnetic background noise level prevails. Difficulties may arise when using Hall-effect sensors, for example, at such electromagnetic background noise levels, since their functional requirements dictate that they be supplied with a most constant possible direct current. However, relatively long current supply lines are typically needed to supply this direct current to the point of measurement. The situation may arise where the electromagnetic background noise level is injected into the power cable, causing the accuracy of the measured values to deteriorate. Another advantage of a conductor loop, respectively of a coil may reside in that it measures the field integral over the conductor loop surface, respectively the coil surface. Such a measured value obtained by "area-based" measurements may be superior to measured values obtained by "point-based" measurements, as are supplied, for example, by a Hall-effect sensor or a magnetoresistive sensor. In particular, it is thereby possible that the positioning of the magnetic-field measuring means need not be considered as precisely when configuring the same. This may lead, under certain circumstances, to a significant improvement in measuring accuracy, particularly in the case of inhomogeneous fields. In the case of synchrotrons, this may lead to a significant improvement in the position and/or focusing of the particle beam. The induction measuring means may preferably be designed as a rigidly configured coil or conductor loop. However, it is also conceivable that the induction measuring means also include a rotary coil or conductor loop that is capable of being set into rotary motion with the aid of a driving device, such as an electromotor.

It may prove to be advantageous for a magnetic-field generating device, in particular one that has an induction measuring means, to include at least one integrator device. Generally, induction measuring means are only able to measure the change in the magnetic field over time, thus $A \propto dB/dt$, A being the measured value of the magnetic-field measuring means. In other words, the existing magnetic field may only be ascertained using a time integration $B=\int Adt$ (starting from an initial value). This may be accomplished with the aid of the integrator device, which may be designed as an analog integrator device, a digital integrator device, or as a combination of an analog and digital integrator device.

The design of a magnetic-field generating device may also provide for at least one magnetic-field measuring means to be configured in the region of at least one pole shoe and/or of at least one yoke. Tests have shown that the values measured at those locations typically correlate best with the magnetic field that is "felt" by the objects present in the magnetic gap, respectively by the objects that are passed through the magnetic gap. Thus, the knowledge of the magnetic field "effectively" being applied may again be more precise. It is possible, in particular, for at least one magnetic-field measuring means to be designed as a conductor loop that wraps at least substantially completely around the particular pole shoe. In the context of a synchrotron (respectively, very generally in the context of a particle beam), the measurement may quasi be "focused" at the virtual path of the particle beam. This is especially true since this is normally located symmetrically within the magnetic gap, relative to the pole shoes and/or the yoke. The particle beam may thereby be directed with a high degree of positional accuracy and/or be very finely focused.

Another advantageous refinement provides for the magnetic-field generating device to have at least one direct magnetic-field measuring means which, in particular, is designed as an NMR probe, as a magnetoresistive measuring element and/or as a Hall-effect sensor. A "direct" magnetic-field measuring means is understood, in particular, to be a measuring means that is able to "directly" and immediately measure the magnitude of the magnetic field, and not only indirectly on the basis of the change in the magnetic field over time. This makes it possible to avoid the offset problems that may arise upon integration of a measurement signal. It may be especially beneficial for such direct magnetic-field measuring means to be provided in addition to induction measuring means. Hall-effect sensors, in particular, should only be used as supplementary magnetic-field measuring means (for example, in addition to a conductor loop). The magnetic-field measuring means may then be used, for example, to compensate for the offset drifts in the induction measuring means (respectively, in the associated integrator devices) that occur over time. Magnetoresistive measuring elements are understood, in particular, to be those measuring elements that have a magnetoresistive material (giant magnetoresistivity). In some instances, a rotatably mounted and driven coil or conductor loop may also be utilized as a direct magnetic-field measuring means. This holds especially when the direction of the magnetic field is constant, respectively is known (in some instances, using measuring methods). If the particular angular position of the rotating coil or conductor loop is also known, the strength of the magnetic field may be measured, for example, based on a parallel position of the normal of the coil and of magnetic field lines during the subsequent 90° rotation of the coil. In this context, the rotational frequency of the coil should preferably be fast relative to the rate of change of the magnetic field. NMR probes are typically only suited for use with dipole magnetic-field generating devices, since inhomogeneous fields, as occur, for example, when working with quadrupole magnetic-field generating devices, are often problematic for NMR probes.

The magnetic-field generating device may be designed, in particular, to include the use of at least one magnetic-field measuring means as a trigger device. In particular, the measured value of a direct measuring means may be used as a "zero position trigger" for an induction measuring means (respectively, for the integrator device used in connection with the induction measuring means). The realization underlying this design is that direct magnetic-field measuring means, which also have the capability to quantitatively measure strong magnetic fields, often age quickly, respectively are subject to significant temperature fluctuations, are expensive, or, however, are relatively large to permit coverage of a large and accurate enough measuring range. However, if direct magnetic-field measuring means are only used to determine the zero crossing of the magnetic field, they may, for the most part, be much simpler in design and normally entail significantly fewer of the other disadvantages referred to. Simple, direct magnetic-field measuring means of this kind normally fully suffice though to prevent a zero line drift of the induction measuring means (respectively, of the integrator device). This applies not only to a zero crossing of the magnetic field, but, analogously, also to a crossing in the case of one (or also a plurality) of defined values of the magnetic field strength and/or in the case of a crossing of the magnetic current intensity through a defined value (such as a magnetic current zero crossing, for example). For example, a direct magnetic-field measuring means, such as a Hall-effect sensor, for instance, could be optimized to a magnetic field strength at which the particle beam is injected into a synchrotron. Since the injection of the particle beam (or also other plateau phases in the case of an acceleration cycle) requires a certain amount of time, it is possible in some instances for direct magnetic-field measuring means to also be used that require a certain amount of time for the measurement, such as NMR probes, for example.

Moreover, in the case of a magnetic-field generating device, it may prove to be advantageous for at least one measurement signal of at least one magnetic-field measuring means to be used as an input signal for controlling at least one magnetic-field generating means of the magnetic-field generating device. This type of design of the magnetic-field generating device not only makes it possible to know the actually prevailing magnetic field, but also to use the knowledge thereby gained to stabilize the magnetic field. For example, the current acting on at least one of the magnetic-field generating means of the magnetic-field generating device may be readjusted in such a way that the desired magnetic field is obtained. Thus, a specific magnetic field and no longer a certain current value—as is customary in known methods heretofore—may be selected as a setpoint value for the magnetic-field generating device. A suitably designed control device may be used, in particular, to control at least one magnetic-field generating means of the magnetic-field generating device. In this context, a separate control device may be used (for example, a single-board computer) or an already present control device may perform this task as well. It would be conceivable, for example, to modify a DCCT control device for that purpose.

In accordance with the present disclosure, a system having at least one magnetic-field generating device is also provided that includes at least one magnetic-field generating device having the above described design. The device in question then features correspondingly the properties and advantages already described.

In particular, it is possible to design the system to include a synchrotron, the synchrotron having at least one magnetic-field generating device that is designed as a dipole magnetic-field generating device and/or as a quadrupole magnetic-field generating device, the at least one magnetic-field generating device including at least one magnetic-field measuring means that is located within a magnetic gap of the at least one magnetic-field generating device, the measured value of the at least one magnetic-field measuring means being used to control and/or readjust at least one magnetic-field generating device, in particular, to control the magnetic-field generating device in which the at least one magnetic-field measuring means is located. In this context, the dipole magnetic-field generating devices are used first and foremost for beam deflection, while the quadrupole magnetic-field generating devices are used first and foremost for focusing the particle beam of the synchrotron. Thus, the quadrupole magnetic-field generating devices may be used to adjust the shape of the ion beam (round, oval, punctual, sheet-like, etc.). Medical applications, such as tumor therapy, in particular, for example, require that both the deflection of the particle beam, as well as the focusing thereof, be exactly reproducible. Any significant deflections may not only cause damage to tissue that is not designated for irradiation, but may also lead to beam loss. The ion beam generated by the synchrotron is normally deflected by deflection magnets into two mutually orthogonal directions (x-direction, y-direction) and to the region to be irradiated (tumor). The depth variation (z-direction) may be performed by suitably adjusting the particle energy. The energy is typically selected in a way that allows the particle beam to lose its main energy (due to what is commonly referred to as the Bragg peak) in the area of the target region (tumor). Generally, the energy of the ion beam must be varied very frequently (due to the varying treatment depth), particularly when what is commonly known as the raster scanning method is used, whereby the ion beam scans the target region in a point-to-point or line-to-line process (if indicated, also repeatedly). Accordingly, the magnetic-field generating devices of the synchrotron must also be variably controlled. In spite of the changing particle energies, the position and focusing of the ion beam must be reproducibly adjustable. This may be advantageously accomplished by the precise adjustability (for example, better than $10^{-4}$, preferably better than $10^{-5}$ of the design value) of the magnetic-field generating devices of the synchrotron. This may be made possible in that a measurement signal generated by at least one magnetic-field measuring device is used to regulate the magnetic-field generating devices. This measurement signal may influence an output signal for controlling a current source of the magnetic-field generating device (respectively, of the magnetic-field generating means, such as, for example, of a normal-conducting coil of the magnetic-field generating device).

It may prove to be particularly advantageous for the system to be at least partially designed as a medical therapeutic device, as a medical diagnostic device, as a tomograph computer, as a nuclear spin tomograph (NMR) and/or as a particle accelerator, in particular, as a linear accelerator and/or as a synchrotron. It is in these machines, in particular, that the advantages that may be obtained by using the above design in accordance with the present disclosure, become clearly evident. It is self-evident that the system may also be used (primarily) for non-medical purposes. Also conceivable, for example, are an at least partial design of the system as an experimental storage ring, an experimental linear accelerator and/or as a spectrometer.

A method is also provided for operating a magnetic-field generating device and/or a system having at least one magnetic-field generating device, in particular a method for operating a magnetic-field generating device having the design discussed above and/or a system having the design discussed above, whereby, during the operation of the magnetic-field generating device, the magnetic field measured by the magnetic-field measuring means is used for controlling at least one magnetic-field generating means of the magnetic-field generating device, in particular, for controlling a power supply device of the magnetic-field generating means. Such a method makes it possible, in particular, to use the measured values relating to the magnitude of the actually prevailing magnetic field to stabilize the magnetic field. For example, it is possible to readjust the current acting on at least one of the magnetic-field generating means of the magnetic-field generating device in such a way that the desired magnetic field is obtained. Thus, a specific magnetic field strength may be selected as a setpoint value for the magnetic-field generating device and no longer a certain current value, as is customary in known methods heretofore.

In particular, the method may be implemented in such a way that at least one magnetic-field generating means is controlled at least periodically and/or at least regionally and/or at least partially as a function of the magnetic field measured by the magnetic-field measuring means. This corresponds generally to a direct setpoint selection of the magnetic field that is subsequently generated at this strength. This setpoint selection may also be implemented only for specific regions, such as for the magnetic gap, for example. It is also conceivable that the setpoint selection of a specific magnetic field only take place at specific points in time, for example, during the rising and/or trailing ramps, respectively, upon reaching the extraction plateau. A mixed regulation of current intensity and magnetic field may also take place.

In particular, the method may be implemented in such a way that the control is carried out at least periodically and/or at least regionally and/or at least partially in accordance with a control model ascertained in advance that is readjusted at least periodically and/or at least regionally and/or at least partially as a function of the magnetic field measured by the magnetic-field measuring means. This makes it possible, for example, to specify a maximum change in current per unit of time, in order not to overload certain components of the current amplification circuits. It is also possible to design the circuit in a way that will still allow a "classical" operation of the system in the case of a failure of the magnetic-field measuring means. The system may then continue to be operated until it is repaired, even though at a degraded efficiency. Such an enhanced operational reliability is of great value for medical applications, in particular.

Figure 1:
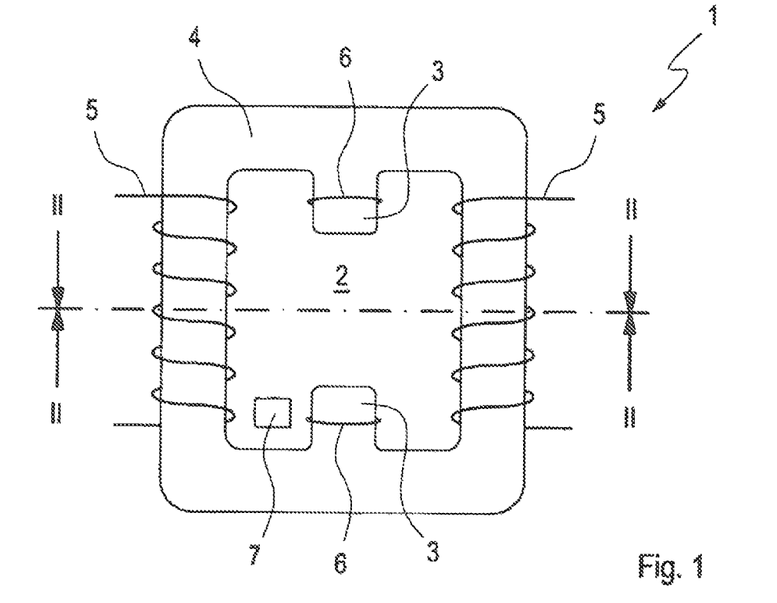
FIG. 1: a dipole magnet for a synchrotron in a schematic plan view from the front.

In a schematic plan view, FIG. 1 shows an exemplary embodiment of a dipole magnet 1 for a synchrotron. Dipole magnets 1 of this kind are used in synchrotrons to deflect the particle beam and thereby force it into a circular path. The beam guide tube, in which a vacuum prevails and the particle beam propagates, is normally configured in center recess 2 of dipole magnet 1.

Discernible directly adjacently to center recess 2 are the two pole shoes 3 of dipole magnet 1. At the rear sides thereof facing away from center recess 2, pole shoes 3 are joined by a yoke 4 of a soft magnetic material. In the exemplary embodiment shown in FIG. 1, a coil 5 is wound around yoke 4 on both sides. Thus, a magnetic field is generated in center recess 2 in response to application of an electric current to coils 5.

Also provided in FIG. 1 in the area of each of pole shoes 3 is a measuring loop 6. Using these measuring loops 6, it is possible to very precisely ascertain the magnetic field prevailing in center recess 2. In this context, tests have shown that it generally suffices for measuring loop 6 to be provided at merely one pole shoe 3. Naturally, it is also fundamentally possible to additionally or alternatively provide one or a plurality of measuring loops 6 in the area of yoke 4 of dipole magnet 1.

Since it is inherent to the measuring principle of measuring loops 6 that they are only able to measure changes in the magnetic fields over time, they are not able to directly measure the strength of a magnetic field. Therefore, to determine the strength of the magnetic field, an additional integrator is provided that integrates the signals coming from measuring loop(s) 6, over time, allowing inferences to be made regarding the strength of the magnetic field. In this context, both analog, as well as numerical integrators may be used.

For example, an ordinary ADC (analog to digital converter) may be used for integration purposes. Output value $B_i$ of the ADC is analyzed in fixed time intervals $\Delta t$, for example. The field strength is then ascertainable from initial value c of the integration plus the sum of all ADC measured values multiplied by $\Delta t$. It holds that $$B(t) = c + \sum_i B_i \Delta t.$$

First tests have shown, however, that better results are presumably obtained by using a U/f converter (voltage-frequency converter). In this context, the coil signal is fed to the U/f converter. Each pulse emitted by the U/f converter then corresponds to a defined field strength increment $\Delta B$. The pulses may only be summed by a counter. Total number $n_i$ of the pulses then corresponds to the actual total field strength variation dB, (an additive constant c still needing to be considered). It holds that $$B(t) = c + \sum_i n_i dB_i.$$

However, regardless of the type of integrator used, a drift in the zero line may generally not be ruled out when measuring loops 6 are (exclusively) used to determine the magnetic field (additive constant).

Additional measures may be taken to also gain control of the zero line drift. Thus, it is possible, for example, to provide for readjustment of the output magnetic field strength. To avoid scatter fluctuations, the signals used for readjustment may be averaged over a plurality of cycles, and/or a plurality of signals may be used for the readjustment. It is possible, for example, to use the zero crossing of the applied voltage as an input signal for the readjustment. Another option provides for using additional measuring sensors 7 to detect the presence of a zero crossing of the magnetic field (or of a very small magnetic field), for example. It is also possible to use the particle beam itself as an adjustment signal. If certain properties are evident in the (extracted) beam, then a readjustment is performed.

It should generally be noted that the output value does not necessarily make it readily feasible to infer an absolute value of the magnetic field. Rather a calibration suffices where the particle beam is used as a calibration standard. If the beam has the desired properties, the magnetic field measurement may then be logged over the entire cycle. This may then be presented in the table of setpoint values. If in a later acceleration cycle, the magnetic field profile deviates from the table of setpoint values, for instance because the accelerator is executing other sequences, then it is the task of the field controller to bring the actual value of the magnetic field to the setpoint value and to reproducibly impart the desired properties to the particle beam. To this end, the current that flows through coils 5 that generate the magnetic field, may be readjusted accordingly. In other words, a magnetic field regulation is performed based on an "in situ" calibration.

In the exemplary embodiment of a dipole magnet 1 illustrated in FIG. 1, an additional sensor 7 provided for readjustment purposes is configured laterally adjacently to one of pole shoes 3 of dipole magnet 1. Thus, sensor 7 is likewise situated outside of center recess 2. In the present context, additional sensor 7 is designed as a Hall-effect sensor 7. Since the Hall-effect sensor is merely used for "zero calibrating" the magnetic field measured value, the configuration of Hall-effect sensor 7 is variable within wide limits. In particular, there is no need for Hall-effect sensor 7 to produce an exact absolute value (apart from the zero crossing in the present exemplary embodiment). Therefore, the Hall-effect sensor may also be positioned in an area that does not necessarily need to be representative for the integral field distribution. Rather, it generally suffices when an "in situ" calibration can be performed. The "zero calibration" is preferably performed in the context of an intermediate flat top of the magnetic field, for example, in the context of the particle injection flat top. Since in the case of an intermediate flat top, the magnetic field remains for some time at a relatively constant magnetic field strength, a somewhat slower measurement process is also possible in some instances. Therefore, slower measuring sensors or measuring methods may be used. It is also possible to use measuring sensors whose accuracy is first derived, for example, from numerical postprocessing (which normally requires a certain amount of time for the requisite calculations). This is the case, for example, when working with commercial, high-precision Hall-effect sensors, respectively with commercial, high-precision magnetoresistive sensors.

Figure 2:
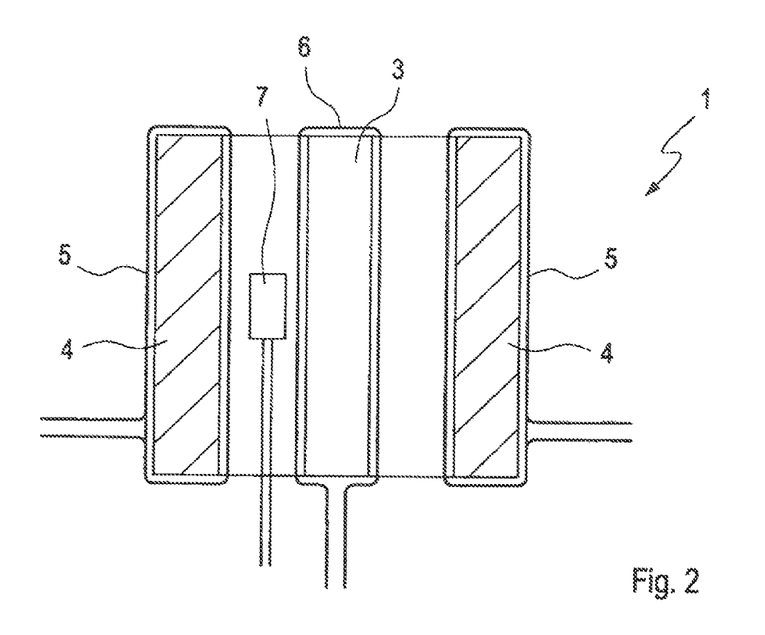
FIG. 2: a schematic cross section through the dipole magnet illustrated in FIG. 1.

Dipole magnet 1 shown in FIG. 1 is discernible in FIG. 2 in a schematic plan view of a cross-sectional area II-II. The section extends along plane II-II marked in FIG. 1. It is readily discernible in the cross-sectional view that conductor loop 6 surrounds entire pole shoe 3 of dipole magnet 1. Thus, measuring loop 6 registers the entire magnetic field acting on the particles of the particle beam as it propagates through dipole magnet 1.

Figure 3:
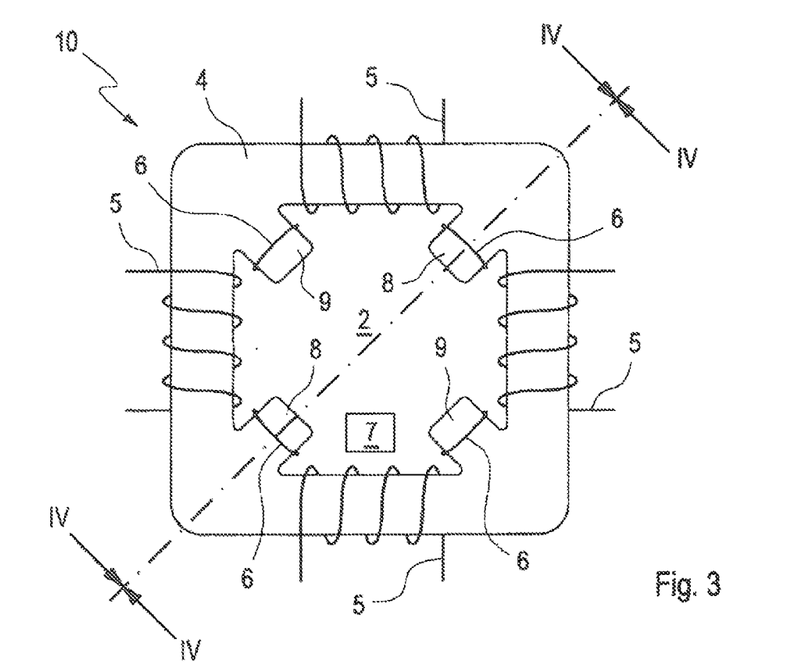
FIG. 3: a quadrupole magnet for a synchrotron in a schematic plan view from the front.

FIG. 3 depicts the situation for a quadrupole magnet 10. In synchrotrons, quadrupole magnets 10 are used for focusing the particle beam. A quadrupole magnet 10 has altogether four pole shoes 8, 9, namely, in each case, two pole shoes 8, 9 having the same polarity. In this context, pole shoes 8, 9 having the same polarity are configured oppositely from each other in each case. For beam focusing in the x- and y-direction (plane perpendicular to the direction of motion of the particles), it is necessary to use at least two quadrupole magnets 10 that are rotated by 90° from each other.

In the exemplary embodiment illustrated in FIG. 3, a measuring loop 6 is wound around each of pole shoes 8, 9 of quadrupole magnet 10. Tests have shown that it normally suffices when only two of the four pole shoes 8, 9 are provided with a measuring loop 6. High-quality measuring results are obtained, in particular, when two pole shoes 8, 9, each having the same polarity (magnetic north pole, respectively magnetic south pole), are provided with a measuring loop 6.

It may also prove to be sufficient for merely one single pole shoe 8, 9 to be provided with a measuring loop 6. In addition—analogously to dipole magnet 1 shown in FIG. 1—a Hall-effect sensor 7 may also be provided in the present case.

Figure 4:
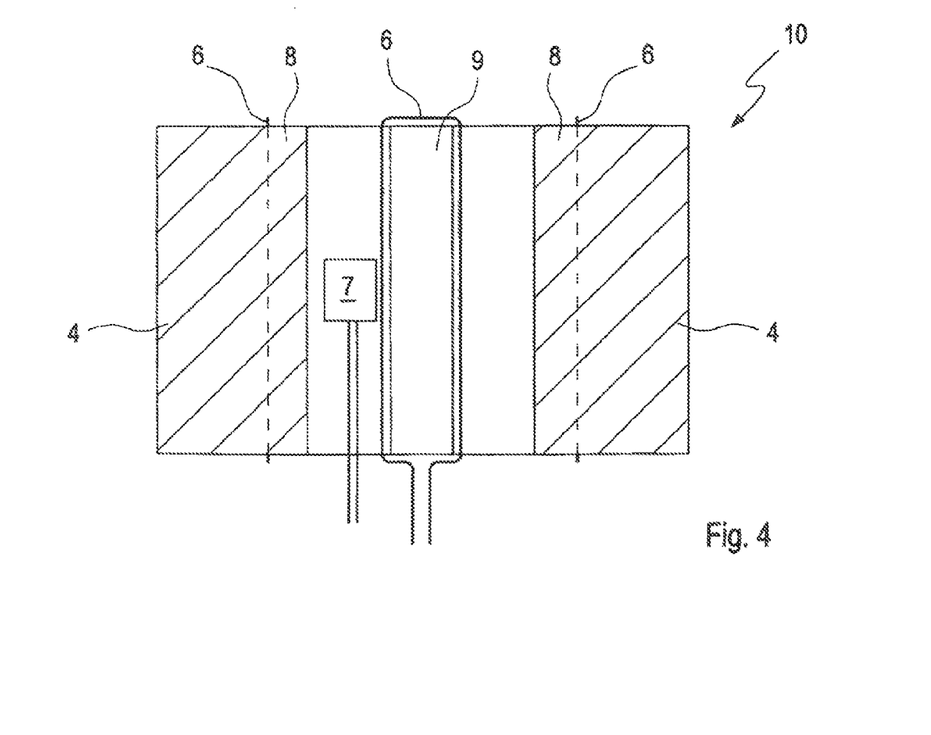
FIG. 4: a schematic cross section through the quadrupole magnet illustrated in FIG. 3.

FIG. 4 illustrates a schematic plan view of quadrupole magnets 10 shown in FIG. 3, the plan view extending from plane of cross-section IV-IV marked in FIG. 3.

Figure 5:
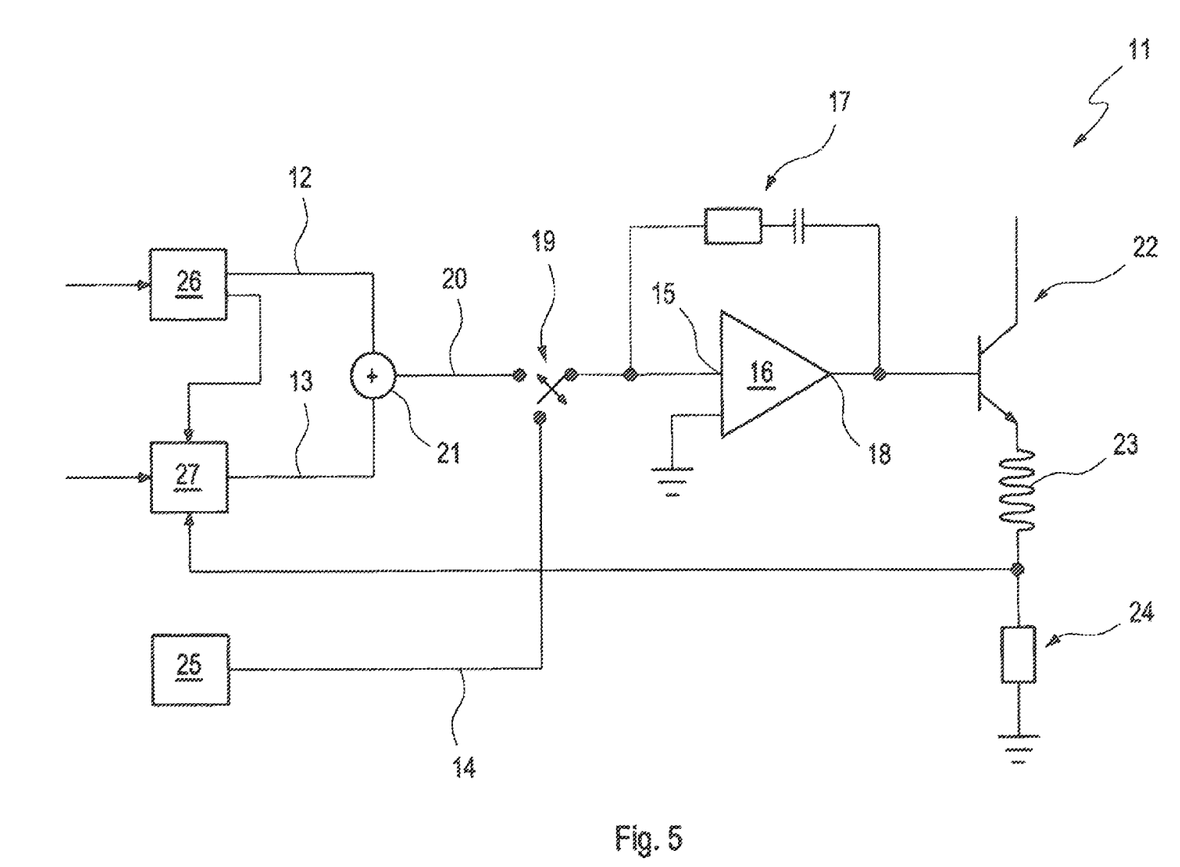
FIG. 5: a circuit diagram for a control circuit for a magnet.

FIG. 5 illustrates an exemplary embodiment of an electronic circuit arrangement 11 which makes it possible to use the strength of the magnetic field ascertained with the aid of measuring loops 6 and Hall-effect sensor 7 to control a magnet (for example, dipole magnet 1 or quadrupole magnet 10).

Output 18 of operational amplifier 16 controls a power amplification stage 22 that supplies electric current to one or more excitation coils 5, 23 of a dipole magnet 1 or quadrupole magnet 10.

Non-inverting input 15 of operational amplifier 16 is optionally connected by a switch 19 to two different input signals 14, 20. In addition, output 18 of operational amplifier 16 is connected via a high-pass filter 17 to non-inverting input connection 15 in order to suppress an unwanted high-frequency oscillation tendency.

Power amplification stage 22 is only able to be appropriately readjusted when the values generated by the measuring sensors (in the present case, by measuring loops 6 and Hall-effect sensor 7) are provided accurately and rapidly enough. In this context, the limiting value for "accurately and rapidly enough" depends on the particular intended purpose. Thus, for example, a therapeutic use of ion beams for tumor therapy generally requires relatively exact limiting values. Again in this context, the limiting values for a tumor therapy using the raster scanning method are more exact than in the case of an irradiation using shaping masks.

In accordance with the present state of knowledge, a relative stability of the magnetic fields of $10^{-4}$ (both for dipole fields, as well as for quadrupole fields) is safe and sufficient for the raster scan irradiation of tumors. However, this relative condition must be fulfilled for all beam energies that are used. Thus, in relative terms, magnetic fields having a strength of 10% of the maximum design value must be stable to $10^{-4}$ which corresponds to an accuracy of $10^{-5}$ in relation to the maximum design value. If this accuracy is not attained, the readjustment does not produce an adequate improvement over the actual state. On the contrary, the particle beam quality may even deteriorate.

With regard to the rate at which the measured values need to be present for the magnetic field, previous experiments have shown that the measured values should be available within 30 μs, preferably within 20 μs, most preferably within 10 μs.

It should be mentioned that a necessary consequence of the speed requirement is also that certain methods that can be readily applied to a laboratory measurement, cannot be used for an "on-line" readjustment. For example, an "on line" operation does not permit a subsequent correction of a drift.

In normal operation, selector switch 19 is set in such a way that first control signal 14 based on the measured magnetic field is applied to non-inverting input 15 of operational amplifier 16. First control signal 14 is supplied by a first electronic processing circuit 25 which processes the values measured by measuring loops 6 and Hall-effect sensor 7 in the manner already described above.

Should a disturbance arise when generating first control signal 14 (for example, because the electronic processing circuit detects an inconsistency in the measurement signals of measuring loops 6 and/or of Hall-effect sensor 7), the system may then continue to be used in an emergency operation. To this end, selector switch 19 is switched over, so that output signal 20 of signal summer 21 is now applied to non-inverting input 15 of operational amplifier 16. Output signal 20 of signal summer 21 mainly follows output signal 12 of an electronic control circuit 26. Based on the current operating state of the synchrotron, electronic control circuit 26 generates output signal 12, which correlates with the current intensity to be applied to the magnet(s) (dipole magnets 1 and/or quadrupole magnets 10), based on a theoretical model and with the aid of a characteristic map ascertained in advance in a measurement laboratory that reproduces the relation between the applied current intensity and the generated magnetic field.

In addition, another signal 13 is additionally applied to signal summer 21. Signal 13 is generated by a DCCT (direct current to current transformer) 27. It takes the value of current intensity 24 actually measured in excitation coil 23 and compares it to setpoint selection 12 of electronic control circuit 26. Based on this comparison between setpoint value 12 and actual value 24 of the current flowing in excitation coil 23, power amplifier 22 is readjusted accordingly.

In emergency operation, the control corresponds to the control as is customary in known methods. This means that it is still necessary to use a "chimney" or training cycles in order to achieve sufficient accuracy for therapeutic purposes. Nevertheless, an enhanced operational reliability of the entire system is provided during the emergency operation.

Figure 6:
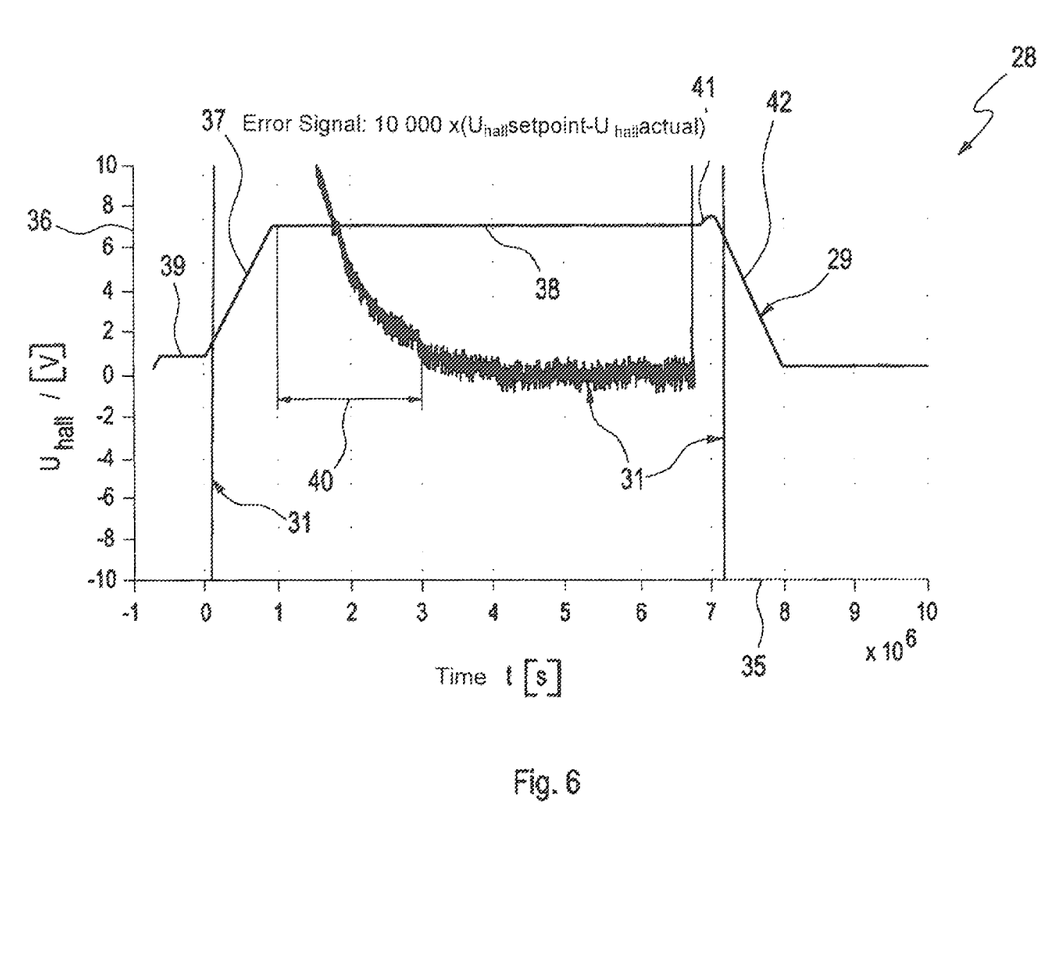
FIG. 6: an example of the behavior of a magnet having a model-based control.
Figure 7:
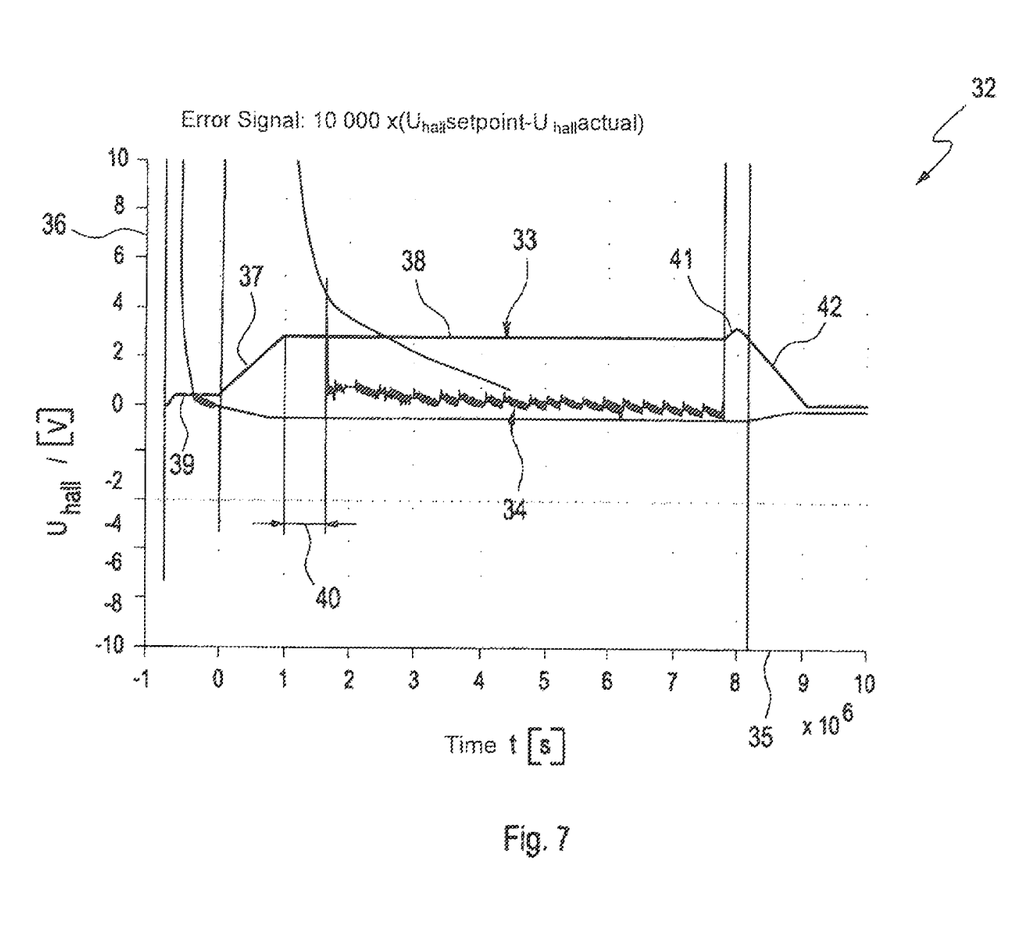
FIG. 7: an example of the behavior of a magnet having magnetic field control.

For comparison purposes, FIG. 6 and FIG. 7 show, respectively, an acceleration cycle 28 in emergency operation (FIG. 6), as well as an acceleration cycle 32 in normal operation (FIG. 7). The time is plotted in seconds in each case on abscissa 35. On the one side, setpoint field 29, 33 of the particular magnet is represented (in any given units) on ordinate 36. Moreover, difference 31, 34 between the setpoint field and the actual field is represented along ordinate 36, the difference being increased by factor $10^4$ to make it more discernible.

Acceleration cycle 28, 32 begins in each case with injection phase 39, in which a pre-accelerated particle beam (for example, a carbon ion beam) is injected into synchrotron 75.

This is followed by acceleration phase 37, during which the particles are accelerated. During acceleration phase 37, the magnetic field generated by magnets 1, 10 must increase with rising particle energy. As is discernible from FIGS. 6 and 7, at that time, difference 31, 34 between setpoint value and actual value is particularly great. However, this is not problematic since, at that point in time, a synchrotron 75 is operated under operating conditions that ensure a high level of inherent stability of particle beam 74.

Plateau phase 38, during which the process of extracting the particles from synchrotron 75 is to take place, begins at the end of acceleration phase 37. However, to be able to extract the particles, synchrotron 75 must first be transferred into an operating state in which particle beam 74 has only a low inherent stability. However, this requires that difference 31, 34 between the setpoint value and actual value of the magnetic field be very small. Otherwise, a beam loss may occur. However, even if no beam loss occurs, a greater difference 31, 34 between the setpoint value and actual value of the magnetic field would be problematic since it could result, inter alia, in the particles of particle beam 74 not being uniformly extracted (substantially constant number of extracted particles per unit of time), but with a pronounced peak in the extraction rate. However, this is undesirable for medical applications, particularly since the therapeutic results thereby degrade. Other properties of the particle beam may also deteriorate, which is likewise undesirable.

For this reason, in emergency operation, one must initially still wait for a relatively long stabilization phase 40 to elapse until difference 31, 34 between the setpoint value and the actual value of the magnetic field is small enough. The time period of stabilization phase 40 must be great enough that the dynamic disturbance effects, which are substantially caused by eddy currents, are able to sufficiently decay. Generally, the time duration of stabilization phase 40 is a multiple of the time constant of the yoke material. In the present case, a time duration of approximately two seconds must elapse (given a total cycle duration of approximately 10 seconds). Only subsequently thereto may the process of extracting the particle beam begin. It is immediately apparent that the efficiency of the system is degraded by the necessity of having to wait for a plurality of seconds to elapse.

On the other hand, stabilization phase 40 is significantly shortened in normal operation 32 (FIG. 7). Thus, the process of extracting particle beam 74 may be begun much earlier.

In the exemplary embodiments illustrated in FIGS. 6 and 7, plateau phase 38 is followed by what is generally referred to as a "chimney" 41, both in emergency operation 28, as well as in normal operation 32. This means that the magnetic field is increased again until the soft magnetic material of yoke 4 of magnets 1, 10 is in a saturation state. As previously mentioned, this is necessary in order to produce defined initial conditions for yoke material 4 for next acceleration cycle 28, 32. Following "chimney" 41, the magnetic field is reduced 42 to the level of injection phase 39.

It should be noted that acceleration cycles 28, 32 illustrated in FIGS. 6 and 7 were measured in a prototype arrangement. Actual test results suggest that it is probably feasible for "chimney" 41 to be completely or at least partially omitted in normal operation 32 (FIG. 7). It is immediately apparent that it is thereby possible to economize again on the energy and dead time of the system. This is particularly the case when an operation is to be carried out at low energies. Acceleration phase 37 is then significantly shorter; however, the time required for a "chimney" is prolonged accordingly.

Figure 8:
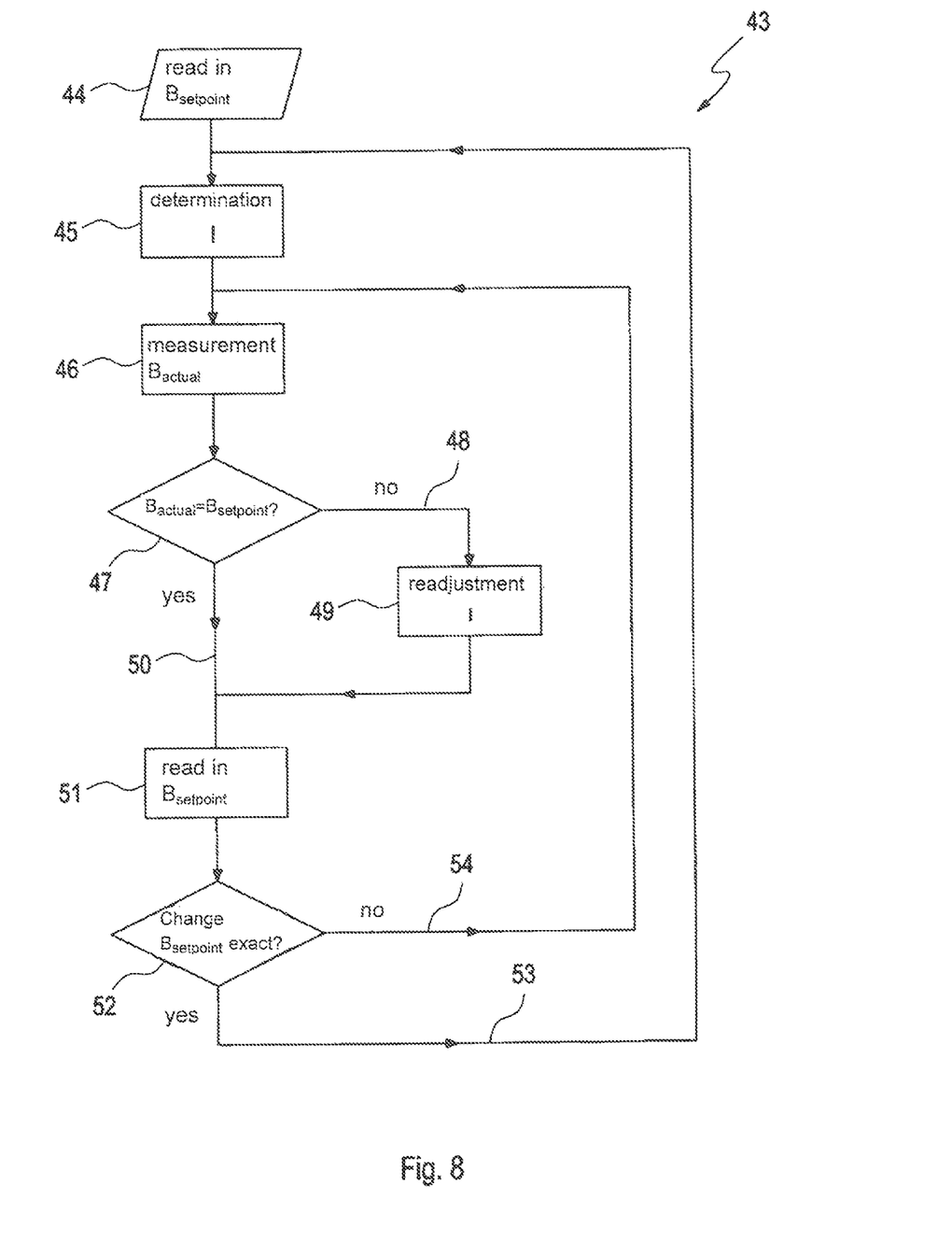
FIG. 8: an exemplary embodiment of a magnetic field regulation method.

FIG. 8 shows a flow diagram 43 of one possible method for regulating the magnetic field of an accelerator magnet (for example, a dipole magnet 1 or a quadrupole magnet 10) for a synchrotron 75 used for treating tumors.

At the beginning of the process, an initial setpoint value $B_{setpoint}$ for the magnetic field strength to be generated by magnet 1, 10 is input in a first step 44.

Based on the setpoint value of magnetic field strength $B_{setpoint}$, initial parameters for magnet 1, 10, in particular for a current intensity I to be initially adjusted, are ascertained in a second step 45. This may be accomplished, for example, using a "look-up table" that is created in advance. The thus ascertained values are applied to magnets 1, 10. A certain period of time is preferably allowed to elapse until magnet 1, 10 stabilizes. The time period that must elapse may, for example, likewise be stored in the "look-up table." It is likewise possible that the current intensity controller (DCCT controller) outputs a signal indicating that it has reached setpoint current intensity I.

Magnetic field $B_{actual}$ ascertained with the aid of the magnetic field sensors is subsequently measured in a further step 46. The thus obtained measured value $B_{actual}$ is subsequently compared to setpoint value $B_{setpoint}$. If values $B_{setpoint}$ and $B_{actual}$ deviate from one another, then the method branches to a first branch 48. In this branch 48, magnetic current intensity I is readjusted 49 based on the difference between $B_{setpoint}$ and $B_{actual}$. On the other hand, if values $B_{setpoint}$ and $B_{actual}$ coincide, readjustment step 49 is skipped, and operational sequence 50 advances directly to next step 51.

In subsequent step 51, the now current setpoint value $B_{setpoint}$ of the magnetic field strength is input. It is subsequently checked 52 whether new setpoint value $B_{setpoint}$ of the magnetic field strength deviates substantially 53 or only slightly (if at all) 54 from the previous setpoint value $B_{setpoint}$ of the magnetic field strength. Accordingly, the operational sequence branches. The criterion "substantial deviation," respectively, "slight deviation" may, for example, be based on an absolute change in setpoint value $B_{setpoint}$ of the magnetic field strength or on a relative change in setpoint value $B_{setpoint}$ of the magnetic field strength.

If setpoint value $B_{setpoint}$ of the magnetic field strength does not change or changes only slightly, operational sequence 54 branches back to the beginning of readjustment loop 46, 47, 49, thus, to input 46 of actual value $B_{actual}$ of the magnetic field strength.

However, if setpoint value $B_{setpoint}$ of the magnetic field strength changes significantly, then operational sequence 53 jumps further back. At this point, an initial magnetic current value I is ascertained 45 once more. Only subsequently thereto is readjustment loop 46, 47, 49 carried out again.

It is naturally also possible to provide a termination criterion for operational sequence 43, for example, when the system on which the process is carried out, is to be switched off.

For example, if a termination signal is present, the magnetic current intensity may be driven to zero.

Figure 9:
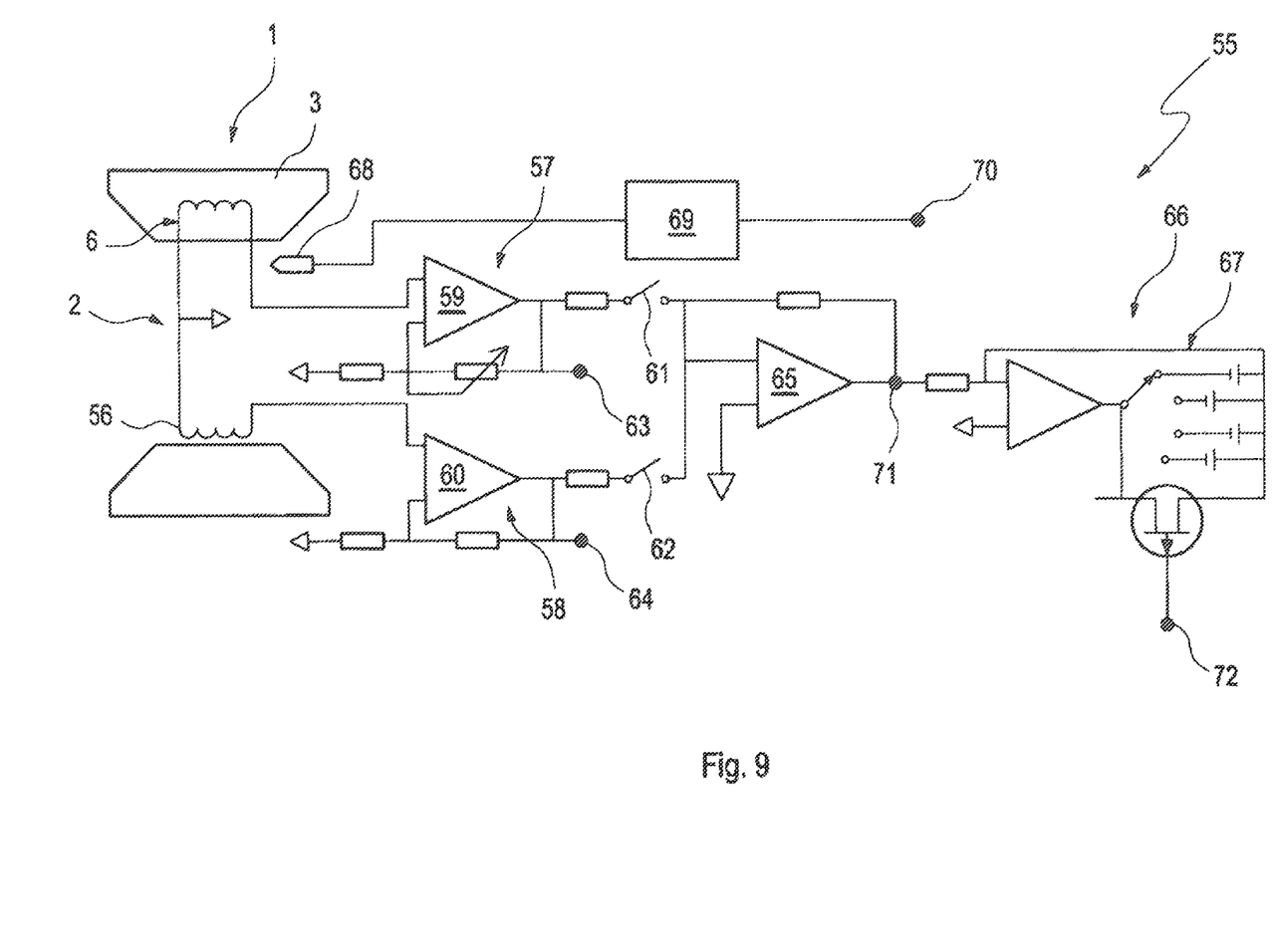
FIG. 9: an exemplary embodiment of a design for calibrating a measuring loop of a magnet.

A schematic circuit diagram 55 of a switch for calibrating a measuring loop ("pick-up coil") 6 is illustrated in FIG. 9. Measuring loop 6 is configured around pole shoe 3 of dipole magnet 1 that is only schematically illustrated in FIG. 9. In addition, a reference coil 56 is configured in center recess 2 of dipole magnet 1. This reference coil 56 may, in particular, be located in an area where particle beam 74 propagates (or, if indicated, where a different object is located) in the completely set-up state of system 73. The measured values recorded by measuring loops 6, 56 are first fed to two amplifier units 57, 58, one amplifier unit 57, 58 being assigned to one measuring loop 6, 56 in each case. Besides an operational amplifier 59, 60, amplifier units 57, 58 also have additional components (for example, resistors), which may be used to adjust amplifier units 57, 58. In addition, a signal pick-off point 63, 64 is provided in each case in connection with amplifier units 57, 58.

A post-amplifier stage 65 is connected downstream of amplifier units 57, 58. Output signals 63, 64 of amplifier units 57, 58 may be selectively supplied via switches 61, 62 to post-amplifier stage 65. Output signal 71 of post-amplifier stage 65 is fed, in turn, to an integrator stage 66 in which signal 71 is integrated. Integrator stage 66 outputs the integral value as output signal 72. In this context, an adjusting device 67 may be used to adjust integrator stage 66 to different amplification stages. Furthermore, output signal 72 of integrator stage 66 may be zeroized by adjusting device 67.

Also configured in central recess 2 of dipole magnet 1 is a Hall-effect sensor 68, whose output signal is processed via a sensor electronics 69, so that a magnetic field strength value 70 is output at output 70 of sensor electronics 69.

When reference coil switch 62 is closed (measuring loop switch 61 open), output value 70 of the Hall-effect sensor and output value 72 of reference coil 56 may be compared to one another. In the process, amplifier unit 58 of reference coil 56 may be properly calibrated. Similarly, when measuring loop switch 61 is closed (reference coil switch 62 open), amplifier unit 59 of measuring loop 6 may be calibrated.

If both measuring loop switch 61 and reference coil switch 62 are closed, then the difference (note different preceding sign!) in output signals 63, 64 from measuring loop 6 and reference coil 56 are output to post-amplifier unit 65 and amplified by the same. The difference between the two measured values 63, 64 may now be quantitatively and qualitatively precisely examined. Tests have shown that the two output signals 63, 64 from measuring loop 6 and reference coil 56 correlate very well with each other. In particular, the signal of measuring loop 6 is exact enough to be suited for readjusting coil current I of electrical coils 5 of magnets 1, 10.

Figure 10:
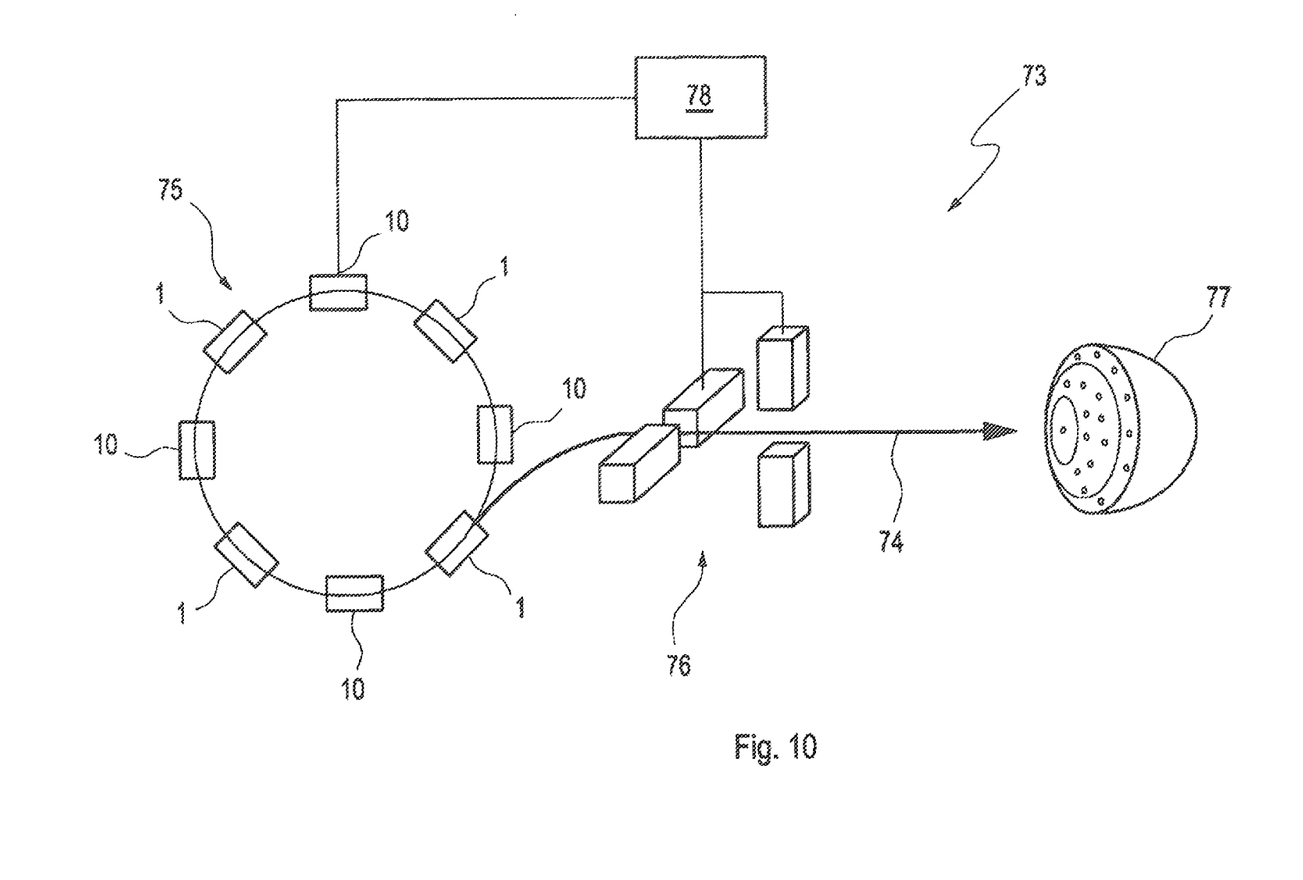
FIG. 10: an exemplary embodiment of a therapeutic system.

A therapeutic system 73 for tumor therapy that is performed with the aid of a particle beam 74 is sketched in FIG. 10. Particle beam 74 is generated by a synchrotron 75 that is only schematically sketched here. Synchrotron 75 has a multiplicity of dipole magnets 1, as well as of quadrupole magnets 10. Particle beam 74 extracted from synchrotron 75 is deflected via a deflection magnet pair 76 into two planes (x-direction, y-direction), which extend perpendicularly to one another, and is directed to an irradiation region 77. Irradiation region 77 may, in particular, be a tumor to be irradiated of a patient. While deflection magnet pair 76 carries out the positioning of particle beam 74 onto irradiation region 77 in the x-direction and y-direction, the energy of particle beam 74 is used for the positioning in the z-direction. This places the Bragg peak of particle beam 74 in such a way that the main energy loss occurs in irradiation region 77. The treatment process follows in that irradiation region 77 is scanned in a raster-like manner. To this end, the beam energy of particle beam 74 (and thus the control of synchrotron 75), as well as the deflection of particle beam 74 in deflection magnet pair 76 must be varied accordingly. This is undertaken by a control computer 78 into which a corresponding treatment plan is programmed.

If magnets 1, 10 of synchrotron 75 are designed in accordance with the present disclosure and/or controlled in accordance with the method of the present disclosure, it is possible to significantly enhance the effectiveness of the treatment process. In particular, the treatment duration may be shortened, which, besides facilitating a more rapid treatment that is advantageous for the patient, in particular, also permits a greater number of treatments.

While the disclosure has been described with reference to the particular embodiments thereof, it will be understood by those having ordinary skill in the art that various changes may be made therein without departing from the scope and spirit of the disclosure. Further, the present disclosure is not limited to the embodiments described herein; reference should be had to the appended claims.

The invention claimed is:

1. A magnetic-field generating device comprising:
   at least one magnetic-field generator configured to generate a magnetic field so as to provide at least one magnetic gap for receiving objects upon which the magnetic field acts, the at least one magnetic field generator being included in a synchrotron and being a dipole or quadrupole magnetic-field generating device; and
   at least one magnetic-field measuring device disposed within a measuring-device receiving region outside of the magnetic gap, the at least one magnetic-field measuring device being configured to provide at least one measurement signal useable as an input signal for controlling the at least one magnetic-field generator.

2. The magnetic-field generating device as recited in claim 1, wherein the magnetic-field generator is configured to at least periodically generate a time-variant magnetic field.

3. The magnetic-field generating device as recited in claim 1, wherein the magnetic-field generator includes at least one of a dipole magnetic-field generating device and a quadrupole magnetic-field generating device.

4. The magnetic-field generating device as recited in claim 1, wherein the at least one magnetic-field measuring device is configured to operate by induction.

5. The magnetic-field generating device as recited in claim 4, wherein the at least one magnetic-field measuring device includes at least one of a conductor loop and a coil.

6. The magnetic-field generating device as recited in claim 4, further comprising at least one integrator device.

7. The magnetic-field generating device as recited in claim 1, wherein the at least one magnetic-field measuring device is a direct magnetic-field measuring device.

8. The magnetic-field generating device as recited in claim 7, wherein the at least one magnetic-field measuring device is least one of an NMR sensor, a magnetoresistive measuring element, and a Hall-effect sensor.

9. The magnetic-field generating device as recited in claim 5, wherein the at least one magnetic-field measuring device is configured as a trigger device.

10. The magnetic-field generating device as recited in claim 1, wherein the at least one magnetic-field generator is included in at least one of a medical therapeutic device, a medical diagnostic device, a tomograph computer, a nuclear spin tomograph and a particle accelerator.

11. A magnetic-field generating device comprising:
at least one magnetic-field generator configured to generate a magnetic field so as to provide at least one magnetic gap for receiving objects upon which the magnetic field acts; and
at least one magnetic-field measuring device disposed within a measuring-device receiving region outside of the magnetic gap, the at least one magnetic-field measuring device being configured to provide at least one measurement signal useable as an input signal for controlling the at least one magnetic-field generator, wherein the at least one magnetic-field measuring device is configured to operate by induction and wherein the at least one magnetic-field measuring device is disposed in a region of at least one of a pole shoe and a yoke.

12. The magnetic-field generating device as recited in claim 11, wherein the particle accelerator is at least one of a linear accelerator and a synchrotron.

13. A method for operating a magnetic-field generating device, the method comprising:
generating, by at least one magnetic-field generator, a magnetic field so as to provide at least one magnetic gap configured to receive objects upon which the magnetic field acts;
measuring, by at least one magnetic-field measuring device disposed within a measuring-device receiving region outside of the magnetic gap, the magnetic field during operation of the magnetic-field generating device; and
controlling, by the magnetic-field measured by the magnetic field measuring device, the at least one magnetic field generator at least one of periodically, regionally, and partially in accordance with a control model as a function of the magnetic field measured by the magnetic-field measuring device.

14. The method as recited in claim 13, wherein the step of controlling the at least one magnetic-field generator includes controlling a power supply of the magnetic-field generator.

15. A method for operating a magnetic-field generating device, the method comprising:
generating, by at least one magnetic-field generator, a magnetic field so as to provide at least one magnetic gap configured to receive objects upon which the magnetic field acts;
measuring, by at least one magnetic-field measuring device disposed within a measuring-device receiving region outside of the magnetic gap, the magnetic field during operation of the magnetic-field generating device; and
controlling, by the magnetic-field measured by the magnetic field measuring device, the at least one magnetic field generator wherein the step of controlling the at least one magnetic-field generator is carried out at least one of periodically regionally and partially in accordance with a control model ascertained, in advance of the controlling and that is readjusted at least one of periodically, regionally and partially as a function of the magnetic-field measured by the magnetic-field measuring device.

* * * * *